US010208171B2

(12) United States Patent
Lee et al.

(10) Patent No.: US 10,208,171 B2
(45) Date of Patent: Feb. 19, 2019

(54) PREPARATION METHOD OF SUPERABSORBENT POLYMER AND SUPERABSORBENT POLYMER PREPARED THEREBY

(71) Applicant: LG Chem, Ltd., Seoul (KR)

(72) Inventors: Yong Hun Lee, Daejeon (KR); Chang Sun Han, Daejeon (KR); Hye Mi Nam, Daejeon (KR); Dong Jo Ryu, Daejeon (KR); Hyemin Lee, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/984,977

(22) Filed: May 21, 2018

(65) Prior Publication Data

US 2018/0265653 A1 Sep. 20, 2018

Related U.S. Application Data

(62) Division of application No. 15/124,156, filed as application No. PCT/KR2015/005956 on Jun. 12, 2015.

(30) Foreign Application Priority Data

Jun. 13, 2014 (KR) ........................ 10-2014-0072343

(51) Int. Cl.
| | |
|---|---|
| *C08F 2/10* | (2006.01) |
| *C08J 3/075* | (2006.01) |
| *C08J 3/24* | (2006.01) |
| *C08F 265/06* | (2006.01) |
| *A61L 15/24* | (2006.01) |
| *A61L 15/60* | (2006.01) |
| *C08J 3/12* | (2006.01) |
| *B01J 20/26* | (2006.01) |
| *C08J 7/12* | (2006.01) |

(52) U.S. Cl.
CPC .............. *C08J 3/245* (2013.01); *A61L 15/24* (2013.01); *A61L 15/60* (2013.01); *B01J 20/267* (2013.01); *C08F 2/10* (2013.01); *C08F 265/06* (2013.01); *C08J 3/075* (2013.01); *C08J 3/12* (2013.01); *C08J 3/24* (2013.01); *C08J 3/247* (2013.01); *C08J 7/12* (2013.01); *B01J 2220/68* (2013.01); *C08F 2810/20* (2013.01); *C08J 2333/02* (2013.01); *C08J 2351/06* (2013.01); *C08J 2400/14* (2013.01); *C08J 2433/02* (2013.01); *C08J 2471/02* (2013.01)

(58) Field of Classification Search
None
See application file for complete search history.

(56) References Cited

U.S. PATENT DOCUMENTS

| | | | | |
|---|---|---|---|---|
| 4,446,261 A * | 5/1984 | Yamasaki | ................. | C08F 2/08 523/202 |
| 5,633,316 A * | 5/1997 | Gartner | ................... | A61L 15/48 525/329.1 |
| 5,760,080 A * | 6/1998 | Wada | ................ | A61F 13/15203 524/559 |
| 5,883,158 A * | 3/1999 | Nambu | ................... | A61L 15/60 523/408 |
| 6,187,841 B1 * | 2/2001 | Tanaka | ................ | C04B 24/2641 524/3 |
| 6,376,581 B1 | 4/2002 | Tanaka et al. | | |
| 6,723,797 B2 * | 4/2004 | Fujii | ........................ | C08F 8/18 119/166 |
| 7,173,086 B2 * | 2/2007 | Smith | ................... | C08F 220/06 524/430 |
| 2001/0006267 A1 * | 7/2001 | Harada | ....................... | C08J 3/12 264/140 |
| 2003/0087993 A1 * | 5/2003 | Nishikawa | .......... | C04B 24/2647 524/2 |
| 2007/0015860 A1 * | 1/2007 | Frank | ....................... | B01J 20/26 524/450 |
| 2007/0078231 A1 * | 4/2007 | Shibata | ................... | A61L 15/24 525/329.7 |
| 2009/0131255 A1 * | 5/2009 | Ikeuchi | ................. | C08F 220/06 502/402 |
| 2009/0208441 A1 * | 8/2009 | Couturier | .............. | C04B 24/243 424/78.03 |
| 2010/0075844 A1 * | 3/2010 | Loeker | .................... | A61L 15/60 502/402 |
| 2014/0058048 A1 * | 2/2014 | Won | ....................... | B01J 20/267 525/384 |
| 2015/0099624 A1 * | 4/2015 | Lee | ....................... | C08F 220/28 502/402 |
| 2017/0015798 A1 * | 1/2017 | Lee | .......................... | C08J 3/245 |

FOREIGN PATENT DOCUMENTS

| | | |
|---|---|---|
| CN | 1154953 A | 7/1997 |
| CN | 1829765 A | 9/2006 |

(Continued)

OTHER PUBLICATIONS

International Search Report from PCT/KR2015/005956, dated Sep. 30, 2015.

(Continued)

*Primary Examiner* — Peter A Salamon
(74) *Attorney, Agent, or Firm* — Lerner, David, Littenberg, Krumholz & Mentlik, LLP

(57) ABSTRACT

Provided are a preparation method of a superabsorbent polymer, and a superabsorbent polymer prepared thereby. The preparation method of the superabsorbent polymer according to the present disclosure enables preparation of the superabsorbent polymer which is excellent in absorption properties such as centrifuge retention capacity and absorbency under pressure, and also has improved permeability. In addition, the preparation method exhibits excellent operability during the preparation (in particular, surface cross-linking of the polymer) and excellent productivity due to low production of coarse particles and fine particles.

5 Claims, No Drawings

(56) References Cited

FOREIGN PATENT DOCUMENTS

| | | |
|---|---|---|
| CN | 101220159 A | 7/2008 |
| EP | 0937736 A2 | 8/1999 |
| EP | 1721663 A1 | 11/2006 |
| JP | S56161408 A | 12/1981 |
| JP | S57158209 A | 9/1982 |
| JP | S57198714 A | 12/1982 |
| JP | H02115201 A | 4/1990 |
| JP | H0328202 A | 2/1991 |
| JP | H07278225 A | 10/1995 |
| JP | H11140193 A | 5/1999 |
| JP | H11140193 A * | 5/1999 ............. A61L 15/60 |
| JP | 2003335970 | 11/2003 |
| KR | 100195778 B1 | 6/1999 |
| KR | 100247526 B1 | 3/2000 |
| KR | 100371649 B1 | 5/2003 |
| KR | 20070037423 A | 4/2007 |
| KR | 20120054836 A | 5/2012 |
| KR | 20130120300 A | 11/2013 |

OTHER PUBLICATIONS

Odian, "Principles of Polymerization." Second Edition, Copyright 1981 by John Wiley & Sons, Inc., p. 203.
Schwalm, "UV Coatings—Basics, Recent Developments and New Applications." Elsevier Science (Dec. 21, 2006), p. 115.
Third Party Observation from PCT/KR2015/005956, dated Oct. 13, 2016.

* cited by examiner

PREPARATION METHOD OF SUPERABSORBENT POLYMER AND SUPERABSORBENT POLYMER PREPARED THEREBY

CROSS-REFERENCE TO RELATED APPLICATION

This application is a divisional of U.S. application Ser. No. 15/124,156, filed Sep. 7, 2016 which is a national phase entry under 35 U.S.C. § 371 of International Application No. PCT/KR2015/005956, filed Jun. 12, 2015, which claims priority from Korean Patent Application No. 10-2014-0072343, filed Jun. 13, 2014. The disclosures of which are incorporated herein by reference.

TECHNICAL FIELD

The present disclosure relates to a preparation method of a superabsorbent polymer, and a superabsorbent polymer prepared thereby.

BACKGROUND OF ART

A superabsorbent polymer (SAP) is a synthetic polymeric material capable of absorbing moisture from about 500 to 1000 times its own weight, and is also called a SAM (Super Absorbency Material), an AGM (Absorbent Gel Material), etc. Since superabsorbent polymers started to be practically applied in sanitary products, now they are being widely used not only for hygiene products such as disposable diapers for children, etc., but also for water retaining soil products for gardening, water stop materials for civil engineering and construction, sheets for raising seedlings, fresh-keeping agents for food distribution fields, or the like.

As a preparation process for such superabsorbent polymers, a process of reverse phase suspension polymerization or a process of solution polymerization has been known. Of them, preparation of the superabsorbent polymer by reverse phase suspension polymerization is disclosed in, for example, Japanese Patent Laid-open Publication Nos. S56-161408, S57-158209, S57-198714, etc. Further, preparation of the superabsorbent polymer by the solution polymerization additionally includes a thermal polymerization method in which a water-containing gel polymer is polymerized while being broken and cooled in a kneader equipped with a plurality of shafts, and a photo-polymerization method in which an aqueous solution with a high concentration is irradiated with UV rays onto a belt to be polymerized and dried at the same time.

In the products made of superabsorbent polymers, permeability is an index of determining fluidity of a liquid to be absorbed. That is, the liquid cannot flow readily through the superabsorbent polymer with low permeability. Permeability may differ depending on particle size distribution of crosslinked polymers, particle shape, the connectedness of the open pores between particles, surface modification of the swollen gel, etc.

As one of the methods of increasing permeability of the superabsorbent polymers, there is a method of performing a surface crosslinking reaction after polymer polymerization. In this regard, a technology of adding an inorganic filler together with a surface crosslinking agent, a technology of coating the surface of the superabsorbent polymer with a polymer such as polyamine, etc., has been suggested.

However, permeability of the superabsorbent polymer may be improved by these methods, but there is a limitation in that centrifuge retention capacity (CRC) and absorbency under pressure (AUP) of the superabsorbent polymer become relatively low. Therefore, there is a trade-off between permeability of the superabsorbent polymer and absorption properties such as centrifuge retention capacity, absorbency under pressure, etc. Accordingly, there is an urgent demand for a technology capable of improving these physical properties at the same time.

DETAILED DESCRIPTION OF THE INVENTION

Technical Problem

The present disclosure provides a preparation method capable of obtaining a superabsorbent polymer which is excellent in absorption properties such as centrifuge retention capacity and absorbency under pressure and that also has improved permeability.

Further, the present disclosure provides a superabsorbent polymer prepared by the above method.

Technical Solution

According to the present disclosure, provided is a preparation method of a superabsorbent polymer, the method including:

forming a water-containing gel polymer by performing thermal polymerization or photopolymerization of a monomer composition including water-soluble ethylene-based unsaturated monomers and a polymerization initiator;

drying the water-containing gel polymer;

pulverizing the dried polymer; and performing a surface-crosslinking reaction by mixing the pulverized polymer with a surface crosslinking solution including a polycarboxylic acid-based copolymer having repeating units represented by the following Chemical Formula 1-a and Chemical Formula 1-b:

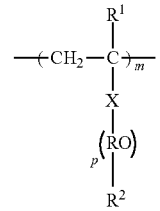
[Chemical Formula 1-a]

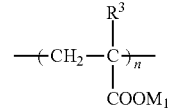
[Chemical Formula 1-b]

wherein, in Chemical Formula 1-a and 1-b, $R^1$, $R^2$, and $R^3$ are each independently hydrogen or an alkyl group having 1 to 6 carbon atoms, RO is an oxyalkylene group having 2 to 4 carbon atoms, $M^1$ is hydrogen or a monovalent metal or non-metal ion, X is —COO—, an alkyloxy group having 1 to 5 carbon atoms, or an alkyldioxy group having 1 to 5 carbon atoms, m is an integer of 1 to 100, n is an integer of 1 to 1000, and p is an integer of 1 to 150, and provided that there are two or more of p, two or more repeating (—RO—)s may be the same as or different from each other.

Here, the polycarboxylic acid-based copolymer may include two or more of different repeating units represented by Chemical Formula 1-b.

The polycarboxylic acid-based copolymer may be mixed in an amount of 0.001 to 5% by weight, based on 100 parts by weight of the pulverized polymer.

Further, the polycarboxylic acid-based copolymer may have a weight average molecular weight of 500 to 1,000,000.

Further, the drying of the water-containing gel polymer may be performed at a temperature of 120° C. to 250° C.

Further, the pulverizing of the dried polymer may be performed so that the pulverized polymer has a particle size of 150 μm to 850 μm.

Further, the surface crosslinking reaction may be performed at a temperature of 100° C. to 250° C.

Further, the surface crosslinking solution may include one or more crosslinking agents selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol, trimethylol propane, pentaerythritol, sorbitol, calcium hydroxide, magnesium hydroxide, aluminum hydroxide, iron hydroxide, calcium chloride, magnesium chloride, aluminum chloride, and iron chloride.

Meanwhile, according to the present disclosure, a superabsorbent polymer including a crosslinked polymer formed by polymerization and internal crosslinking of the water-soluble ethylene-based unsaturated monomers and the polycarboxylic acid-based copolymer represented by Chemical Formula 1, which is present on the crosslinked polymer, is provided.

The superabsorbent polymer may have liquid permeability (saline flow conductivity, SFC) of $10 \times 10^{-7}$ cm$^3$*s/g to $150 \times 10^{-7}$ cm$^3$*s/g, centrifuge retention capacity (CRC) of 20 g/g to 40 g/g, absorbency under pressure (AUP) of 15 g/g to 30 g/g, and permeability dependent absorption under pressure (gravimetric determination of permeability dependent absorption under pressure, PDAUP) of 10 g/g to 25 g/g.

Advantageous Effects

A preparation method of a superabsorbent polymer according to the present disclosure enables preparation of the superabsorbent polymer which is excellent in absorption properties such as centrifuge retention capacity and absorbency under pressure, and also has improved permeability. In addition, the preparation method exhibits excellent operability in a high-speed mixer during the preparation (in particular, surface crosslinking of the polymer) and excellent productivity due to low production of coarse particles and fine particles.

DETAILED DESCRIPTION OF THE EMBODIMENTS

Hereinafter, a preparation method of a superabsorbent polymer according to embodiments of the present disclosure and a superabsorbent polymer prepared thereby will be described.

The terminology used herein is for the purpose of describing exemplary embodiments only and is not intended to limit the present invention. The singular forms used herein may be intended to include the plural forms as well, unless the context clearly indicates otherwise. It will be understood that the term "include" or "contain", used herein, specifies stated features, regions, integers, steps, operations, elements, or components, but does not preclude the addition of other features, regions, integers, steps, operations, elements, or components thereof.

Studies of the present inventors regarding a superabsorbent polymer demonstrated that when a polycarboxylic acid-based copolymer having the following repeating units is added to a surface crosslinking agent during a surface crosslinking reaction of polymer particles, a superabsorbent polymer having excellent absorption properties and improved permeability may be obtained.

One of the reasons for this effect seems to be that the polycarboxylic acid-based copolymer improves dispersibility or coating property of the surface crosslinking agent for the polymer particles, and therefore the surface crosslinking reaction more uniformly occurs.

Furthermore, when the polycarboxylic acid-based copolymer is applied, operability of a mixer is improved during the surface crosslinking process, and production of coarse particles and fine particles is inhibited after the surface crosslinking process, thereby obtaining advantageous effects in terms of process operation and productivity.

I. Preparation Method of Superabsorbent Polymer

According to an aspect of the present disclosure, provided is a preparation method of a superabsorbent polymer, the method including:

forming a water-containing gel polymer by performing thermal polymerization or photopolymerization of a monomer composition including water-soluble ethylene-based unsaturated monomers and a polymerization initiator;

drying the water-containing gel polymer;

pulverizing the dried polymer; and performing a surface-crosslinking reaction by mixing the pulverized polymer with a surface crosslinking solution including a polycarboxylic acid-based copolymer having repeating units represented by the following Chemical Formula 1-a and Chemical Formula 1-b:

[Chemical Formula 1-a]
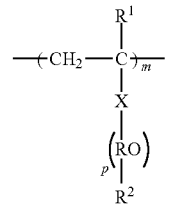

[Chemical Formula 1-b]
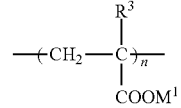

wherein, in Chemical Formula 1-a and 1-b, $R^1$, $R^2$, and $R^3$ are each independently hydrogen or an alkyl group having 1 to 6 carbon atoms, RO is an oxyalkylene group having 2 to 4 carbon atoms, $M^1$ is hydrogen or a monovalent metal or non-metal ion, X is —COO—, an alkyloxy group having 1 to 5 carbon atoms, or an alkyldioxy group having 1 to 5 carbon atoms, m is an integer of 1 to 100, n is an integer of 1 to 1000, and p is an integer of 1 to 150, and provided that there are two or more of p, two or more repeating (—RO—)s may be the same as or different from each other.

Hereinbelow, each step that may be included in the preparation method of the superabsorbent polymer according to an embodiment will be described.

(1) Forming of Water-Containing Gel Polymer

First, the preparation method of the superabsorbent polymer includes forming the water-containing gel polymer by performing thermal polymerization or photopolymerization of the monomer composition including water-soluble ethylene-based unsaturated monomers and the polymerization initiator.

The water-soluble ethylene-based unsaturated monomer included in the monomer composition may be an arbitrary monomer commonly used in the preparation of the superabsorbent polymer.

A non-limiting example of the water-soluble ethylene-based unsaturated monomer may be a compound represented by the following Chemical Formula 2:

  [Chemical Formula 2]

wherein $R^1$ is an alkyl group containing an unsaturated bond and having 2 to 5 carbon atoms, and $M^1$ is a hydrogen atom, a monovalent metal, a divalent metal, an ammonium group, or an organic amine salt.

Preferably, the monomer may be one or more selected from the group consisting of acrylic acid and methacrylic acid, and monovalent metal salts, divalent metal salts, ammonium salts, and organic amine salts of these acids.

As such, when acrylic acid or a salt thereof is used as the water-soluble ethylene-based unsaturated monomer, it is advantageous in that a superabsorbent polymer having improved absorbency is obtained.

In addition, as the monomer, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, (meth)acrylamide, N-substituted (meth)acrylate, 2-hydroxyethyl(meth)acrylate, 2-hydroxypropyl (meth)acrylate, methoxy polyethylene glycol(meth)acrylate, polyethylene glycol(meth)acrylate, (N,N)-dimethylaminoethyl(meth)acrylate, (N,N)-dimethylaminopropyl(meth)acrylamide, etc. may be used.

Here, the water-soluble ethylene-based unsaturated monomers may be those having acidic groups which are at least partially neutralized. Preferably, the monomers may be those partially neutralized with an alkali substance such as sodium hydroxide, potassium hydroxide, ammonium hydroxide, or the like.

In this regard, a degree of neutralization of the monomer may be about 40 mol % to 95 mol %, about 40 mol % to 80 mol %, or about 45 mol % to 75 mol %. The range of the neutralization degree may vary depending on the final physical properties. An excessively high degree of neutralization causes the neutralized monomers to be precipitated, and thus polymerization may not readily occur, whereas an excessively low degree of neutralization not only deteriorates the absorbency of the polymer but also endows the polymer with hard-to-handle properties, such as of elastic rubber.

Further, the concentration of the water-soluble ethylene-based unsaturated monomer in the monomer composition may be properly controlled, in consideration of a polymerization time and reaction conditions, and the concentration may preferably be 20% by weight to 90% by weight, or 40% by weight to 65% by weight, which is for using the gel effect during the polymerization reaction in a high-concentration aqueous solution to eliminate a need for removing the unreacted monomer after the polymerization and also for improving pulverization efficiency upon a subsequent pulverization process of the polymer.

However, if the concentration of the monomer is too low, the yield of the superabsorbent polymer may become low. On the contrary, if the concentration of the monomer is too high, there is a process problem that a part of the monomers is precipitated, or pulverization efficiency is lowered upon pulverization of the polymerized water-containing gel polymer, and the physical properties of the superabsorbent polymer may be reduced.

Meanwhile, the monomer composition may include a polymerization initiator generally used in the preparation of the superabsorbent polymer. Non-limiting examples of the polymerization initiator may include a thermal polymerization initiator or a photo-polymerization initiator depending on a polymerization method. However, even though the photo-polymerization is performed, a certain amount of heat is generated by UV irradiation or the like, and is also generated with an exothermic polymerization reaction. Therefore, the thermal polymerization initiator may be further included.

Here, the photo-polymerization initiator may be, for example, one or more compounds selected from the group consisting of benzoin ether, dialkyl acetophenone, hydroxyl alkylketone, phenyl glyoxylate, benzyl dimethyl ketal, acyl phosphine, and α-aminoketone. As a specific example of acyl phosphine, commercial Lucirin TPO, namely, 2,4,6-trimethyl-benzoyl-trimethyl phosphine oxide, may be used. More various photo-polymerization initiators are well disclosed in "UV Coatings: Basics, Recent Developments and New Applications (Elsevier, 2007)" written by Reinhold Schwalm, p 115, which may be served as a reference.

Further, the thermal polymerization initiator may be one or more compounds selected from the group consisting of persulfate-based initiators, azo-based initiators, hydrogen peroxide, and ascorbic acid. Specific examples of the persulfate-based initiators may include sodium persulfate ($Na_2S_2O_8$), potassium persulfate ($K_2S_2O_8$), ammonium persulfate (($NH_4)_2S_2O_8$), or the like. Further, specific examples of the azo-based initiators may include 2,2-azobis(2-amidinopropane)dihydrochloride, 2,2-azobis-(N,N-dimethylene) isobutyramidine dihydrochloride, 2-(carbamoylazo)isobutyronitrile, 2,2-azobis(2-[2-imidazoline-2-yl]propane) dihydrochloride, 4,4-azobis-(4-cyanovaleric acid), or the like. More various thermal polymerization initiators are well-disclosed in "Principle of Polymerization (Wiley, 1981)" written by Odian, p 203, which may be served as a reference.

The polymerization initiator may be added at a concentration of about 0.001% by weight to 1% by weight, based on the monomer composition. That is, if the concentration of the polymerization initiator is too low, the polymerization rate becomes low and thus a large amount of residual monomers may be undesirably extracted from the final product. On the contrary, if the concentration of the polymerization initiator is too high, the polymer chains constituting the network become short, and thus the content of water-soluble components is increased and physical properties of the polymer may deteriorate such as a reduction in absorbency under pressure.

Meanwhile, the monomer composition may further include a crosslinking agent ("internal crosslinking agent") to improve physical properties of the polymer by polymerization of the water-soluble ethylene-based unsaturated monomer. The crosslinking agent is used for internal crosslinking of the water-containing gel polymer, and is separately used, independent of a crosslinking agent ("surface crosslinking agent") for surface crosslinking of the water-containing gel polymer.

As the internal crosslinking agent, any compound is possible as long as it enables introduction of crosslinkage upon polymerization of the water-soluble ethylene-based unsaturated monomers. Non-limiting examples of the internal crosslinking agent may include multifunctional crosslinking agents, such as N,N'-methylenebisacrylamide, trimethylolpropane tri(meth)acrylate, ethylene glycol di(meth)acrylate, polyethylene glycol(meth)acrylate, propylene glycol di(meth)acrylate, polypropylene glycol(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triarylamine, ethylene glycol diglycidyl ether, propylene glycol, glycerin, or ethylene carbonate, which may be used alone or in combination of two or more thereof, but are not limited thereto.

The internal crosslinking agent may be added at a concentration of about 0.001% by weight to 1% by weight, based on the monomer composition. That is, if the concentration of the internal crosslinking agent is too low, the polymer may undesirably have a low absorption rate and low gel strength. On the contrary, if the concentration of the internal crosslinking agent is too high, the polymer may have low absorption ability, which is not preferred for an absorbent.

In addition, the monomer composition may further include an additive such as a thickener, a plasticizer, a preservation stabilizer, an antioxidant, etc., if necessary.

Further, the raw materials such as the above-described monomers, polymerization initiator, internal crosslinking agent, etc. may be dissolved in a solvent, and thus be prepared in the form of a solution of the monomer composition.

In this regard, as the solvent, any solvent may be used without limitations in the constitution as long as it is able to dissolve the above raw materials. For example, water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof may be used.

The formation of the water-containing gel polymer by polymerizing the monomer composition may be performed by a general polymerization method, and the process is not particularly limited. Non-limiting examples of the polymerization method are largely classified into the thermal polymerization and the photo-polymerization according to the polymerization energy source, and the thermal polymerization may be carried out in a reactor like a kneader equipped with agitating spindles and the photo-polymerization may be carried out in a reactor equipped with a movable conveyor belt.

For example, the monomer composition is injected into a reactor like a kneader equipped with the agitating spindles, and thermal polymerization is performed by providing hot air thereto or heating the reactor so as to obtain the water-containing gel polymer. In this regard, the water-containing gel polymer may have a size of centimeters or millimeters when it is discharged from the outlet of the reactor, according to the type of agitating spindles equipped in the reactor. Specifically, the water-containing gel polymer may be obtained in various forms according to the concentration of the monomer composition fed thereto, the feeding speed, or the like, and the water-containing gel polymer having a (weight average) particle size of 2 mm to 50 mm may be generally obtained.

As another example, when the photo-polymerization of the monomer composition is carried out in a reactor equipped with a movable conveyor belt, the water-containing gel polymer may be obtained as a sheet. In this regard, the thickness of the sheet may vary according to the concentration of the monomer composition fed thereto and the feeding speed, and the polymer sheet is preferably controlled to have a thickness of 0.5 cm to 5 cm in order to uniformly polymerize the entire sheet and secure production speed.

The water-containing gel polymer formed by the above method may have a water content of about 40% by weight to 80% by weight. The "water content", as used herein, means a water weight in the total weight of the water-containing gel polymer, which is obtained by subtracting the weight of the dry polymer from the weight of the water-containing gel polymer.

Specifically, the water content is defined as a value calculated by measuring the weight loss according to evaporation of water in the polymer during the drying process of increasing the temperature of the polymer with infrared heating. In this regard, the drying conditions may be determined as follows: the temperature may be increased from room temperature to about 180° C. and then the temperature may be maintained at 180° C., and the total drying time may be determined as 20 min, including 5 min for the temperature rising step.

(2) Drying of Water-Containing Gel Polymer

The preparation method of the superabsorbent polymer includes drying the water-containing gel polymer which is formed by the above described step.

If necessary, the method may further include (coarsely) pulverizing the water-containing gel polymer before the drying, in order to increase efficiency of the drying.

A non-limiting example of a pulverizing device applicable to the coarse pulverization may include a vertical pulverizer, a turbo cutter, a turbo grinder, a rotary cutter mill, a cutter mill, a disc mill, a shred crusher, a crusher, a chopper, a disc cutter, etc.

In this regard, the coarse pulverization may be performed so that the water-containing gel polymer has a particle size of about 2 mm to about 10 mm. That is, to increase the drying efficiency, the water-containing gel polymer is pulverized so that it preferably has a particle size of 10 mm or less. However, excessive pulverization may cause agglomeration between particles, and therefore the water-containing gel polymer is pulverized so that it preferably has a particle size of 2 mm or more.

When the coarse pulverization is performed before the drying of the water-containing gel polymer, the polymer may stick to the surface of the pulverizing device because it has a high water content. In order to minimize this phenomenon, steam, water, a surfactant, an anti-agglomeration agent for fine particles such as clay or silica, etc.; a thermal polymerization initiator such as a persulfate-based initiator, an azo-based initiator, hydrogen peroxide, and ascorbic acid; or a crosslinking agent such as an epoxy-based crosslinking agent, a diol-based crosslinking agent, a crosslinking agent including 2-functional or 3 or more-functional acrylate, or a mono-functional compound including a hydroxyl group may be added during the coarse of pulverization, if necessary.

Meanwhile, the drying of the water-containing gel polymer immediately after coarse pulverization or polymerization may be performed at a temperature of 120° C. to 250° C., or 150° C. to 200° C., or 160° C. to 180° C. (in this regard, the temperature means the temperature of the heating medium provided thereto for drying, or the internal temperature of the drying reactor including the heating medium and the polymer during the drying process).

If the drying temperature is low, and therefore the drying time becomes long, physical properties of the final polymer may be deteriorated. In order to prevent this problem, the drying temperature is preferably 120° C. or higher.

In addition, when the drying temperature is higher than necessary, only the surface of the water-containing gel polymer is dried, and thus there is a concern about generation of fine powder during the subsequent pulverization process and deterioration of the physical properties of the polymer finally formed. In order to prevent this problem, therefore, the drying temperature is preferably 250° C. or lower.

In this regard, the drying time in the drying is not particularly limited, but may be controlled to 20 to 90 min at the above drying temperature, in consideration of the process efficiency.

A drying method for the drying may also be a method commonly used in the drying process of the water-containing gel polymer, and there is no limitation in the constitution. Specifically, the drying may be carried out by a method of supplying hot air, irradiating infrared rays, irradiating microwaves, irradiating ultraviolet rays, or the like.

The water content of the polymer dried by the above method may be about 0.1% by weight to about 10% by weight. In other words, if the water content of the polymer is less than 0.1% by weight, production costs may be increased due to excessive drying and degradation of the crosslinked polymer may undesirably occur. If the water content of the polymer is more than 10% by weight, defective products may be undesirably produced in the subsequent process.

(3) Pulverizing of Dried Polymer

The preparation method of the superabsorbent polymer includes pulverizing the polymer which is dried by the above-described step.

The pulverization is for optimizing the surface area of the dried polymer, and may be performed so that the pulverized polymer has a particle size of 150 μm to 850 μm. In this regard, a pulverization device applicable to the pulverization for such particle size may be exemplified by a pin mill, a hammer mill, a screw mill, a roll mill, a disc mill, a jog mill, or the like.

Further, the polymer particles obtained through the pulverization may be selectively size-sorted into the polymer having a particle size of 150 μm to 850 μm, in order to manage physical properties of the superabsorbent polymer finally produced.

(4) Surface Crosslinking Reaction of Pulverized Polymer

The preparation method of the superabsorbent polymer includes surface-crosslinking the polymer which is pulverized by the above-described step.

According to an embodiment, the pulverized polymer before the surface crosslinking reaction may have centrifuge retention capacity (CRC) of 45 g/g or less, for example, 25 g/g to 45 g/g, and a shear modulus of 3500 Pa or more, for example, 3500 Pa to 6500 Pa. The polymer having these physical properties is subjected to a surface crosslinking reaction by mixing the polymer with a surface crosslinking solution, thereby obtaining a superabsorbent polymer having more improved physical properties.

The surface crosslinking reaction is a step of increasing crosslinking density of the surface of the polymer particle, and a solution including the crosslinking agent (surface crosslinking agent) may be mixed with the pulverized polymer to allow the crosslinking reaction.

Here, the kind of the crosslinking agent (surface crosslinking agent) included in the surface crosslinking solution is not particularly limited. Non-limiting examples of the surface crosslinking agent may include one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol trimethylol propane, pentaerythritol, sorbitol, calcium hydroxide, magnesium hydroxide, aluminum hydroxide, iron hydroxide, calcium chloride, magnesium chloride, aluminum chloride, and iron chloride.

In this regard, the content of the surface crosslinking agent may be properly controlled according to the kind of the crosslinking agent or reaction conditions, and the content is preferably 0.001 parts by weight to 5 parts by weight, based on 100 parts by weight of the pulverized polymer. If the content of the surface crosslinking agent is too low, surface crosslinking may hardly occur to deteriorate physical properties of the final polymer. On the contrary, if the surface crosslinking agent is excessively used, excessive surface crosslinking reaction may occur, undesirably leading to deterioration in absorption ability of the polymer.

Particularly, in the present disclosure, a surface crosslinking solution including a polycarboxylic acid-based copolymer having repeating units represented by the following Chemical Formula 1-a and Chemical Formula 1-b may be used, together with the crosslinking agent, in the surface crosslinking reaction:

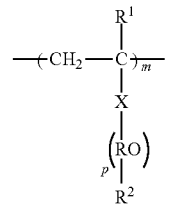

[Chemical Formula 1-a]

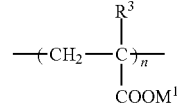

[Chemical Formula 1-b]

wherein, in Chemical Formula 1-a and 1-b, $R^1$, $R^2$, and $R^3$ are each independently hydrogen or an alkyl group having 1 to 6 carbon atoms, RO is an oxyalkylene group having 2 to 4 carbon atoms, $M^1$ is hydrogen or a monovalent metal or non-metal ion, X is —COO—, an alkyloxy group having 1 to 5 carbon atoms, or an alkyldioxy group having 1 to 5 carbon atoms, m is an integer of 1 to 100, n is an integer of 1 to 1000, and p is an integer of 1 to 150, and provided that there are two or more of p, two or more repeating (—RO—)s may be the same as or different from each other.

Here, the polycarboxylic acid-based copolymer may include two or more of different repeating units represented by Chemical Formula 1-b.

The polycarboxylic acid-based copolymer enables the surface crosslinking agent to be uniformly dispersed or coated on the surface of the polymer particles, resulting in a more uniform surface crosslinking reaction.

In particular, the application of the polycarboxylic acid-based copolymer may minimize a reduction of absorption properties of the polymer particles, and may also improve permeability which has a trade-off relationship with the absorption properties.

Furthermore, the application of the polycarboxylic acid-based copolymer may improve operability of a mixer during the surface crosslinking process and may inhibit production of coarse particles and fine particles after the surface crosslinking process, thereby obtaining advantageous effects in terms of process operation and productivity.

According to an embodiment of the present disclosure, it is advantageous in terms of achieving the above-described effect that a random copolymer derived from hydrophilic monomers such as alkoxy polyalkylene glycol mono(meth) acrylic acid ester-based monomers (represented by methoxy polyethylene glycol monomethacrylate (MPEGMAA)) and (meth)acrylic acid ester-based monomers (represented by acrylic acid, (meth)acrylic acid, etc.) is used as the polycarboxylic acid-based copolymer.

According to an embodiment of the present disclosure, to better achieve the addition effect of the polycarboxylic acid-based copolymer, it is preferable that the polycarboxylic acid-based copolymer has a weight average molecular weight of 500 to 1,000,000, or 5000 to 500,000, or 10,000 to 100,000.

Further, the content of the polycarboxylic acid-based copolymer may be properly controlled according to the kind of the copolymer, reaction conditions, etc., and is preferably controlled to 0.001 parts by weight to 5 parts by weight, or 0.01 parts by weight to 3 parts by weight, based on 100 parts by weight of the pulverized polymer. If the content of the polycarboxylic acid-based copolymer becomes too low, the above effect required in the present disclosure may not be sufficiently achieved. In contrast, excessive use of the polycarboxylic acid-based copolymer may undesirably cause a reduction in intrinsic absorption properties of the superabsorbent polymer, surface tension, flowability of powder, etc.

Meanwhile, to perform the surface crosslinking reaction, a method of feeding the surface crosslinking agent and the pulverized polymer to the reactor and mixing them, a method of spraying the surface crosslinking agent to the pulverized polymer, or a method of mixing the pulverized polymer and the surface crosslinking agent while continuously feeding them to a mixer being continuously operated may be used.

When the surface crosslinking solution is added, water may also be added. The addition of water may induce more uniform dispersion of the crosslinking agent, prevent agglomeration of the polymer powder, and optimize the penetration depth of the surface crosslinking agent into the polymer powder. Considering these purposes and effects, the amount of water to be added may be controlled to 0.5 parts by weight to 10 parts by weight, based on 100 parts by weight of the pulverized polymer.

The surface crosslinking reaction may be preferably performed at a temperature of 100° C. to 250° C., and performed sequentially after the drying and pulverizing steps which are performed at a relatively high temperature. In this regard, the surface crosslinking reaction may be performed for 1 min to 120 min, or 1 min to 100 min, or 10 min to 60 min. That is, to induce a minimal surface crosslinking reaction and to prevent a reduction in the physical properties by damage of the polymer particles due to excessive reaction, the surface crosslinking reaction may be performed under the above-described conditions.

II. Superabsorbent Polymer

According to another aspect of the present disclosure, provided is a superabsorbent polymer including a crosslinked polymer formed by polymerization and internal crosslinking of water-soluble ethylene-based unsaturated monomers, and a polycarboxylic acid-based copolymer having repeating units represented by the following Chemical Formula 1-a and Chemical Formula 1-b, which is present on the crosslinked polymer:

[Chemical Formula 1-a]

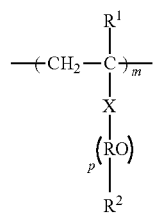

[Chemical Formula 1-b]

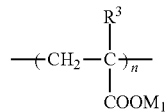

wherein, in Chemical Formula 1-a and 1-b, $R^1$, $R^2$, and $R^3$ are each independently hydrogen or an alkyl group having 1 to 6 carbon atoms, RO is an oxyalkylene group having 2 to 4 carbon atoms, $M^1$ is hydrogen or a monovalent metal or non-metal ion, X is —COO—, an alkyloxy group having 1 to 5 carbon atoms, or an alkyldioxy group having 1 to 5 carbon atoms, m is an integer of 1 to 100, n is an integer of 1 to 1000, and p is an integer of 1 to 150, and provided that there are two or more of p, two or more repeating (—RO—)s may be the same as or different from each other.

Here, the polycarboxylic acid-based copolymer may include two or more of different repeating units represented by Chemical Formula 1-b.

The superabsorbent polymer may include the crosslinked polymer and the polycarboxylic acid-based copolymer present on the crosslinked polymer, and preferably obtained by the method including the above-described processes.

The presence of the polycarboxylic acid-based copolymer included in the superabsorbent polymer may be confirmed by common qualitative or quantitative analysis of the superabsorbent polymer.

The superabsorbent polymer, to which the polycarboxylic acid-based copolymer is applied, may produce a small amount of fine particles, and may exhibit excellent absorption properties such as centrifuge retention capacity and absorbency under pressure, as well as improved permeability.

For example, the superabsorbent polymer may exhibit liquid permeability (SFC) of $10 \times 10^{-7}$ to $150 \times 10^{-7}$ cm$^3$*s/g or $60 \times 10^{-7}$ to $130 \times 10^{-7}$ cm$^3$*s/g. The superabsorbent polymer may have centrifuge retention capacity (CRC) of 20 g/g to 40 g/g or 27 g/g to 35 g/g, as measured according to EDANA WSP 241.2.

The superabsorbent polymer may have absorbency under pressure (AUP) of 15 g/g to 30 g/g or 23 g/g to 27 g/g, as measured according to EDANA WSP 242.2. Further, the superabsorbent polymer may have permeability dependent absorption under pressure (PDAUP) of 10 g/g to 25 g/g or 20 g/g to 25 g/g, as measured according to EDANA WSP 243.1.

Hereinafter, the preferred examples are provided for better understanding. However, these examples are for illustrative purposes only, and the present invention is not intended to be limited by these examples.

Preparation Example 1

A polycarboxylic acid-based copolymer used for a surface crosslinking reaction was prepared by the following method.

To a 3 L, 4-necked flask reactor equipped with a stirrer, a thermometer, a nitrogen inlet, and a circulation condenser, 400 parts by weight of ion exchanged water was fed, and the interior of the reactor was replaced by nitrogen gas under stirring, followed by heating to 75° C. under a nitrogen atmosphere.

2 parts by weight of ammonium persulfate was fed to the reactor, and dissolved completely. Then, a monomer aqueous solution including a mixture of 600 parts by weight of methoxy polyethylene glycol monomethacrylate (average addition molar number of ethylene oxide (EO): about 50 mol), 99.6 parts by weight of methacrylic acid, and 190 parts by weight of water, and a solution mixture of 5 parts by weight of 3-mercaptopropionic acid and 60 parts by weight of water, and 150 parts by weight of 3 wt % ammonium persulfate aqueous solution, were continuously fed at a constant speed for 4 h. After completion of the feeding, 5 parts by weight of 3 wt % ammonium persulfate aqueous solution was fed at once.

Thereafter, the internal temperature of the reactor was raised to 85° C., and maintained at 85° C. for 1 h to complete the polymerization reaction.

The polycarboxylic acid-based copolymer thus prepared was found to have a weight average molecular weight of 40,000, as measured by GPC (gel permeation chromatography).

Preparation Example 2

A polycarboxylic acid-based copolymer (weight average molecular weight of 40,000) was obtained in the same manner as in Preparation Example 1, except that neutralization was performed using a 30 wt % triethanolamine aqueous solution for about 1 h after completion of the polymerization reaction, as in Preparation Example 1.

Preparation Example 3

A polycarboxylic acid-based copolymer (weight average molecular weight of 40,000) was obtained in the same manner as in Preparation Example 2, except that neutralization was performed using a sodium hydroxide aqueous solution, instead of the triethanolamine aqueous solution.

Preparation Example 4

To 3 L, 4-necked flask reactor equipped with a stirrer, a thermometer, a nitrogen inlet, and a circulation condenser, 300 parts by weight of ion exchanged water was fed, and the interior of the reactor was replaced by nitrogen gas under stirring, followed by heating to 75° C. under a nitrogen atmosphere.

2 parts by weight of ammonium persulfate was fed to the reactor, and dissolved completely. Then, a monomer aqueous solution including a mixture of 300 parts by weight of methoxy polyethylene glycol monomethacrylate (average addition molar number of ethylene oxide (EO): about 50 mol), 49.8 parts by weight of methacrylic acid, and 50 parts by weight of water, and a solution mixture of 5 parts by weight of 3-mercaptopropionic acid and 30 parts by weight of water, and 80 parts by weight of 3 wt % ammonium persulfate aqueous solution, were continuously fed at a constant speed for 4 h. After completion of the feeding, 5 parts by weight of 3 wt % ammonium persulfate aqueous solution was fed at once.

Thereafter, the internal temperature of the reactor was raised to 85° C., and maintained at 85° C. for 1 h to complete the polymerization reaction.

The polycarboxylic acid-based copolymer thus prepared was found to have a weight average molecular weight of 45,000, as measured by GPC (gel permeation chromatography).

Preparation Example 5

A polycarboxylic acid-based copolymer (weight average molecular weight of 45,000) was obtained in the same manner as in Preparation Example 4, except that neutralization was performed using the 30 wt % triethanolamine aqueous solution for about 1 h after completion of the polymerization reaction, as in Preparation Example 4.

Preparation Example 6

A polycarboxylic acid-based copolymer (weight average molecular weight of 45,000) was obtained in the same manner as in Preparation Example 5, except that neutralization was performed using the sodium hydroxide aqueous solution, instead of the triethanolamine aqueous solution.

Example 1

About 5.0 g of N,N'-methylenebisacrylamide as an internal crosslinking agent was added to and mixed with about 500 g of acrylic acid, and then about 971.4 g of a 20% sodium hydroxide aqueous solution was added to prepare a monomer composition (degree of neutralization of acrylic acid-based monomer: 70 mol %).

The monomer composition was fed into a 5 L twin-armed kneader equipped with a sigma-type axis, maintained at 40° C., and purged with nitrogen gas for 30 min to eliminate oxygen dissolved in the aqueous solution. About 50.1 g of 0.2 wt % L-ascorbic acid, about 50.5 g of a sodium persulfate aqueous solution, and about 51.0 g of a 2.0 wt % hydrogen peroxide aqueous solution were fed under stirring. The polymerization reaction was initiated in 20 min, and the gel produced was finely divided by way of shear force for 30 min.

The finely divided gel was spread as thick as about 30 mm on a stainless wire gauze having a hole size of 600 μm and dried in a hot air oven at 140° C. for 5 h. The dry polymer thus obtained was ground with a grinder and then size-sorted through an ASTM standard sieve to obtain an absorbent polymer powder having a particle size of 150 μm to 850 μm.

100 g of the polymer powder was uniformly blended with a surface crosslinking solution containing 0.3 g of ethylene glycol diglycidyl ether (surface crosslinking agent), 3 g of methanol, about 0.2 g of the polycarboxylic acid-based copolymer according to Preparation Example 1, and 3 g of water, and then dried in a hot air oven at 140° C. for 30 min. The dry powder thus obtained was size-sorted through an ASTM standard sieve to obtain a superabsorbent polymer having a particle size of 150 μm to 850 μm.

Example 2

A superabsorbent polymer was obtained in the same manner as in Example 1, except that the polycarboxylic acid-based copolymer according to Preparation Example 2 instead of Preparation Example 1 was used.

Example 3

A superabsorbent polymer was obtained in the same manner as in Example 1, except that the polycarboxylic acid-based copolymer according to Preparation Example 3 instead of Preparation Example 1 was used.

Example 4

A superabsorbent polymer was obtained in the same manner as in Example 1, except that the polycarboxylic acid-based copolymer according to Preparation Example 4 instead of Preparation Example 1 was used.

Example 5

A superabsorbent polymer was obtained in the same manner as in Example 1, except that the polycarboxylic acid-based copolymer according to Preparation Example 5 instead of Preparation Example 1 was used.

Example 6

A superabsorbent polymer was obtained in the same manner as in Example 1, except that the polycarboxylic acid-based copolymer according to Preparation Example 6 instead of Preparation Example 1 was used.

Comparative Example 1

A superabsorbent polymer was obtained in the same manner as in Example 1, except that the polycarboxylic acid-based copolymer according to Preparation Example 1 was not used.

Comparative Example 2

A superabsorbent polymer was obtained in the same manner as in Example 1, except that an equal amount of citric acid was added, instead of the polycarboxylic acid-based copolymer according to Preparation Example 1.

Comparative Example 3

A superabsorbent polymer was obtained in the same manner as in Example 1, except that an equal amount of polyoxyethylene sorbitan monooleate was added, instead of the polycarboxylic acid-based copolymer according to Preparation Example 1.

Experimental Example 1

The absorbent polymers prepared in Examples 1 to 6 and Comparative Examples 1 to 3 were subjected to the following experiments, and the results are presented in the following Table 1.

(1) Centrifuge Retention Capacity (CRC)

Centrifuge retention capacity was measured according to EDANA WSP 241.2 for each polymer of the examples and comparative examples. In detail, each polymer W(g) (about 2.0 g) obtained in the examples and comparative examples was uniformly placed into a nonwoven-fabric-made bag, followed by sealing. Then, the bag was immersed in a physiological saline solution (0.9% by weight) at room temperature. After 30 min, the bag was drained at 250 G for 3 min with a centrifuge, and the weight W2 (g) of the bag was then measured. Further, the same procedure was carried out using no polymer, and the resultant weight W1 (g) was measured. Thus, CRC (g/g) was calculated from these weights thus obtained according to the following Equation 1.

$$CRC\ (g/g) = \{(W2 - W1)/(W-1)\} \quad \text{[Equation 1]}$$

(2) Absorbency Under Pressure (AUP)

Absorbency under pressure was measured according to EDANA WSP 242.3 for each polymer of the examples and comparative examples. In detail, a 400 mesh stainless steel net was installed in the bottom of a plastic cylinder having an internal diameter of 60 mm. The superabsorbent polymer W(g) (about 0.90 g) was uniformly scattered on the steel net at room temperature and humidity of 50%, and a piston which may provide a load of 4.83 kPa (0.7 psi) was uniformly put thereon, in which the external diameter of the piston was slightly smaller than 60 mm, there was no appreciable gap between the internal wall of the cylinder and the piston, and the jig-jog of the cylinder was not interrupted. At this time, the weight Wa(g) of the device was measured.

After putting a glass filter having a diameter of 90 mm and a thickness of 5 mm in a petri dish having a diameter of 150 mm, a physiological saline solution composed of 0.90% by weight of sodium chloride was poured in the dish until the surface level became equal to the upper surface of the glass filter. A sheet of filter paper having a diameter of 90 mm was put thereon. The measuring device was put on the filter paper and the solution was absorbed for 1 h under the load. After 1 h, the weight Wb(g) was measured after lifting up the measuring device.

Wa and Wb thus obtained were used to calculate absorbency under pressure (g/g) according to the following Equation 2.

$$AUP\ (g/g) = \{Wb - Wa\}/W \quad \text{[Equation 2]}$$

(3) Liquid Permeability (Saline Flow Conductivity, SFC)

Liquid permeability was measured according to a method disclosed in [0184] to [0189] of column 16 of US Patent Publication No. 2009-0131255.

(4) Permeability Dependent Absorption Under Pressure (Gravimetric Determination of Permeability Dependent Absorption Under Pressure, PDAUP)

Permeability dependent absorption under pressure was measured according to the method of EDANA WSP 243.1. In detail, a 400 mesh stainless steel net was installed in the bottom of a plastic cylinder having an internal diameter of 60 mm. The superabsorbent polymer W(g) (5.0 g) was uniformly scattered on the steel net at room temperature and humidity of 50%, and a piston which may provide a load of 4.83 kPa (0.7 psi) uniformly was put thereon, in which the external diameter of the piston was slightly smaller than 60 mm, there was no appreciable between the internal wall of the cylinder and the piston, and the jig-jog of the cylinder was not interrupted. At this time, the weight W3 (g) of the device was measured.

After putting a glass filter having a diameter of 90 mm and a thickness of 5 mm in a petri dish having a diameter of 150 mm, a physiological saline solution composed of 0.90% by weight of sodium chloride was poured into the dish until the surface level became equal to the upper surface of the glass filter. A sheet of filter paper having a diameter of 90 mm was put thereon. The measuring device was put on the filter paper and the solution was absorbed for 1 h under the load. After 1 h, the weight W4 (g) was measured after lifting up the measuring device. Permeability dependent absorption under pressure was determined by calculating AUP (g/g) according to the following Equation 3.

$$PDAUP\ (g/g) = \{W4 - W3\}/W \quad [\text{Equation 3}]$$

TABLE 1

|  | CRC (g/g) | AUP (g/g) | SFC ($cm^3 \cdot s \cdot 10^{-7}/g$) | PDAUP (g/g) |
|---|---|---|---|---|
| Example 1 | 31.3 | 25.5 | 63 | 21.7 |
| Example 2 | 31.5 | 25.8 | 62 | 22.2 |
| Example 3 | 31.6 | 26.2 | 65 | 23.0 |
| Example 4 | 31.5 | 25.3 | 61 | 21.8 |
| Example 5 | 31.4 | 25.5 | 60 | 22.1 |
| Example 6 | 31.3 | 26.0 | 62 | 23.0 |
| Comparative Example 1 | 30.0 | 24.0 | 52 | 20.1 |
| Comparative Example 2 | 29.6 | 24.2 | 50 | 19.8 |
| Comparative Example 3 | 28.8 | 23.7 | 52 | 19.5 |

Referring to Table 1, the superabsorbent polymers according to the examples were found to have superior absorption properties including centrifuge retention capacity (CRC) and absorbency under pressure (AUP), and superior permeability dependent absorption under pressure (PDAUP), compared to the polymer of Comparative Example 1, indicating that addition of the polycarboxylic acid-based copolymer as in the examples enables the crosslinking agent to be uniformly coated on the surface of polymer particles.

When an organic acid or a non-ionic surfactant was used as in Comparative Example 2 and Comparative Example 3, it was difficult to obtain superabsorbent polymers having the same physical properties as those of the examples.

A high-speed mixer showed excellent operability in the surface crosslinking process according to the examples, compared to those in the comparative examples. Particle size distribution of the products after surface crosslinking in the examples was analyzed. As a result, particles having a size of more than 850 μm and less than 150 μm were produced in a small amount, indicating a relatively narrow particle size distribution.

Example 7

To a 3 L glass reactor equipped with a stirrer, a nitrogen inlet, and a thermometer, 500 g of acrylic acid, 5.5 g of ethoxylated (15) trimethylolpropane triacrylate, and 0.04 g of diphenyl (2,4,6-trimethylbenzoyl)-phosphine oxide were added, and dissolved. Then, 896.4 g of a 24.5% sodium hydroxide aqueous solution was added, and nitrogen was continuously fed to prepare a water-soluble unsaturated monomer aqueous solution. The water-soluble unsaturated monomer aqueous solution was cooled to 70° C. 500 g of this aqueous solution was fed to a stainless steel container having a width of 250 mm, a length of 250 mm, and a height of 30 mm, and UV polymerization was performed by UV radiation (exposure dose: 10 mW/cm$^2$) for 90 s to prepare a water-containing gel polymer.

The water-containing gel polymer thus obtained was pulverized to a size of 2 mm*2 mm, and spread as thick as about 30 mm on a stainless wire gauze having a hole size of 600 μm and dried in a hot air oven at 140° C. for 5 h. The dry polymer thus obtained was ground with a grinder and then size-sorted through an ASTM standard sieve to obtain an absorbent polymer powder having a particle size of 150 μm to 850 μm.

To 100 g of the polymer powder, a surface crosslinking solution containing 1.0 g of ethylene carbonate, 4.0 g of water, about 0.2 g of the polycarboxylic acid-based copolymer according to Preparation Example 1, 0.3 g of oxalic acid, and 0.02 g of silica were added, and uniformly mixed with each other. Then, the mixture was dried in a hot air oven at 180° C. for 60 min. The dry polymer thus obtained was size-sorted through an ASTM standard sieve to obtain a superabsorbent polymer having a particle size of 150 μm to 850 μm.

Example 8

A superabsorbent polymer was obtained in the same manner as in Example 7, except that the polycarboxylic acid-based copolymer according to Preparation Example 2 instead of Preparation Example 1 was used.

Example 9

A superabsorbent polymer was obtained in the same manner as in Example 7, except that the polycarboxylic acid-based copolymer according to Preparation Example 3 instead of Preparation Example 1 was used.

Comparative Example 4

A superabsorbent polymer was obtained in the same manner as in Example 7, except that the polycarboxylic acid-based copolymer according to Preparation Example 1 was not used.

Comparative Example 5

A superabsorbent polymer was obtained in the same manner as in Example 7, except that an equal amount of citric acid was added, instead of the polycarboxylic acid-based copolymer according to Preparation Example 1.

Comparative Example 6

A superabsorbent polymer was obtained in the same manner as in Example 7, except that an equal amount of polyoxyethylene sorbitan monooleate was added, instead of the polycarboxylic acid-based copolymer according to Preparation Example 1.

Comparative Example 7

A superabsorbent polymer was obtained in the same manner as in Comparative Example 4, except that 0.1 g of aluminum sulfate was additionally used in Comparative Example 4.

Experimental Example 2

In order to evaluate physical properties of the absorbent polymers prepared in Examples 7 to 9 and Comparative Examples 5 to 7, the same experiments as in Experimental Example 1 were performed, and the results are presented in the following Table 2.

TABLE 2

|  | CRC (g/g) | AUP (g/g) | SFC (cm$^3$*s*10$^{-7}$/g) | PDAUP (g/g) |
|---|---|---|---|---|
| Example 7 | 27.7 | 24.8 | 105 | 22.2 |
| Example 8 | 27.5 | 25.1 | 110 | 22.4 |
| Example 9 | 27.6 | 25.2 | 121 | 22.4 |
| Comparative Example 4 | 26.3 | 23.5 | 91 | 19.8 |
| Comparative Example 5 | 26.4 | 23.7 | 92 | 19.6 |
| Comparative Example 6 | 26.1 | 23.5 | 92 | 19.3 |
| Comparative Example 7 | 26.3 | 23.8 | 100 | 19.3 |

Referring to Table 2, the superabsorbent polymers according to Examples 7 to 9 showed superior centrifuge retention capacity (CRC), absorbency under pressure (AUP), and permeability dependent absorption under pressure (PDAUP), compared to the polymer of Comparative Example 4, irrespective of the polymerization initiation method or the kind of the surface crosslinking agent for the preparation of absorbent polymer powder.

When an organic acid or a non-ionic surfactant was used as in Comparative Example 5 and Comparative Example 6, it was difficult to obtain superabsorbent polymers having the same physical properties as those of the examples.

Further, although the polymer of Comparative Example 7 was prepared by adding the multivalent metal (aluminium sulfate) during the surface crosslinking, it had poor physical properties, compared to the polymers of the examples.

The invention claimed is:

1. A superabsorbent polymer comprising a crosslinked polymer formed by polymerization and internal crosslinking of water-soluble ethylene-based unsaturated monomers and a polycarboxylic acid-based copolymer having repeating units represented by the following Chemical Formula 1-a and Chemical Formula 1-b, which is present on the crosslinked polymer:

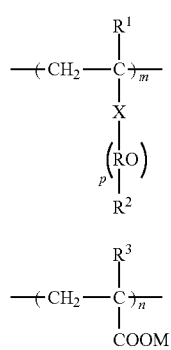

[Chemical Formula 1-a]

[Chemical Formula 1-b]

wherein, in Chemical Formula 1-a and 1-b, $R^1$, $R^2$, and $R^3$ are each independently hydrogen or an alkyl group having 1 to 6 carbon atoms, RO is an oxyalkylene group having 2 to 4 carbon atoms, $M^1$ is hydrogen or a monovalent metal or non-metal ion, X is —COO—, an alkyloxy group having 1 to 5 carbon atoms, or an alkyldioxy group having 1 to 5 carbon atoms, m is an integer of 1 to 100, n is an integer of 1 to 1000, and p is an integer of 1 to 150, and provided that there are two or more of p, two or more repeating (—RO—)s may be the same as or different from each other, wherein the superabsorbent polymer has liquid permeability (SFC) of $60\times10^{-7}$ cm$^3$*s/g to $130\times10^{-7}$ cm$^3$*s/g, centrifuge retention capacity (CRC) of 27 g/g to 35 g/g, absorbency under pressure (AUP) of 23 g/g to 27 g/g, and permeability dependent absorption under pressure (PDAUP) of 20 g/g to 25 g/g.

2. The superabsorbent polymer of claim 1, wherein the polycarboxylic acid-based copolymer has a weight average molecular weight of 500 to 1,000,000 g/mol.

3. The superabsorbent polymer of claim 1, wherein the polycarboxylic acid-based copolymer is a random copolymer derived from methoxy polyethylene glycol monomethacrylate and (meth)acrylic acid.

4. The superabsorbent polymer of claim 1, comprising a crosslinked polymer formed by polymerization and internal crosslinking of water-soluble ethylene-based unsaturated monomers to form a water-containing gel polymer, drying the water-containing gel polymer, pulverizing the dried water-containing gel polymer, and performing a surface crosslinking reaction by mixing the pulverized polymer with a surface crosslinking solution comprising a polycarboxylic acid-based copolymer having repeating units represented by the following Chemical Formula 1-a and Chemical Formula 1-b, which is present on the crosslinked polymer:

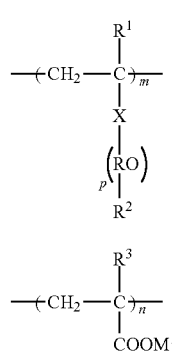

[Chemical Formula 1-a]

[Chemical Formula 1-b]

wherein, in Chemical Formula 1-a and 1-b, $R^1$, $R^2$, and $R^3$ are each independently hydrogen or an alkyl group having 1 to 6 carbon atoms, RO is an oxyalkylene group having 2 to 4 carbon atoms, $M^1$ is hydrogen or a monovalent metal or non-metal ion, X is —COO—, an alkyloxy group having 1 to 5 carbon atoms, or an alkyldioxy group having 1 to 5 carbon atoms, m is an integer of 1 to 100, n is an integer of 1 to 1000, and p is an integer of 1 to 150, and provided that there are two or more of p, two or more repeating (—RO—)s may be the same as or different from each other.

5. The superabsorbent polymer of claim 4, wherein the polycarboxylic acid-based copolymer is present in an amount of 0.001 to 5% by weight, based on 100 parts by weight of the pulverized polymer.

* * * * *